US012685697B2

(12) United States Patent
Neubourg

(10) Patent No.: US 12,685,697 B2
(45) Date of Patent: Jul. 21, 2026

(54) DMS (DERMA MEMBRANE STRUCTURE) IN FOAM CREAMS

(71) Applicant: NEUBOURG SKIN CARE GMBH & CO KG, Greven (DE)

(72) Inventor: Thomas Neubourg, Werne (DE)

(73) Assignee: nsc Pharma GmbH & Co., Greven (DE)

( * ) Notice: Subject to any disclaimer, the term of this patent is extended or adjusted under 35 U.S.C. 154(b) by 225 days.

(21) Appl. No.: 18/610,728

(22) Filed: Mar. 20, 2024

(65) Prior Publication Data

US 2024/0374485 A1     Nov. 14, 2024

Related U.S. Application Data

(63) Continuation of application No. 17/235,152, filed on Apr. 20, 2021, now abandoned, which is a continuation of application No. 16/601,733, filed on Oct. 15, 2019, now abandoned, which is a continuation of application No. 16/270,929, filed on Feb. 8, 2019, now abandoned, which is a continuation of application No. 12/664,732, filed on Dec. 15, 2009, now abandoned, which is a continuation of application No. PCT/EP2008/057791, filed on Jun. 19, 2008.

(30) Foreign Application Priority Data

Jun. 19, 2007     (EP) .................................... 71105571

(51) Int. Cl.
| | |
|---|---|
| A61K 8/04 | (2006.01) |
| A61K 8/02 | (2006.01) |
| A61K 8/36 | (2006.01) |
| A61K 8/37 | (2006.01) |
| A61K 8/55 | (2006.01) |
| A61Q 17/04 | (2006.01) |
| A61Q 19/00 | (2006.01) |
| A61Q 19/10 | (2006.01) |

(52) U.S. Cl.
CPC ............ *A61K 8/046* (2013.01); *A61K 8/0295* (2013.01); *A61K 8/36* (2013.01); *A61K 8/375* (2013.01); *A61K 8/553* (2013.01); *A61Q 17/04* (2013.01); *A61Q 19/005* (2013.01); *A61Q 19/007* (2013.01); *A61Q 19/10* (2013.01); *A61K 2800/33* (2013.01)

(58) Field of Classification Search
CPC ...... A61K 8/046; A61K 8/553; A61K 8/0295; A61K 8/36; A61K 8/375; A61K 2800/33; A61Q 17/04; A61Q 19/005; A61Q 19/007; A61Q 19/10
See application file for complete search history.

(56) References Cited

U.S. PATENT DOCUMENTS

| | | | |
|---|---|---|---|
| 3,793,464 | A | 2/1974 | Rusch |
| 4,200,551 | A | 4/1980 | Orthoefer |
| 4,411,926 | A | 10/1983 | Trumbetas et al. |
| 4,622,074 | A | 11/1986 | Miyoshi et al. |
| 5,120,528 | A | 6/1992 | Chang et al. |
| 5,709,849 | A | 1/1998 | Ito et al. |
| 6,312,703 | B1 | 11/2001 | Orthoefer |
| 6,342,238 | B1 | 1/2002 | Simonnet et al. |
| 6,416,771 | B1 | 7/2002 | Oyama et al. |
| 7,001,604 | B2 | 2/2006 | Albrecht et al. |
| 7,052,716 | B1 | 5/2006 | Lanzendoerfer et al. |
| 2002/0106390 | A1 | 8/2002 | Huglin et al. |
| 2002/0146375 | A1 | 10/2002 | Schreiber et al. |
| 2003/0083210 | A1 | 5/2003 | Goldberg et al. |
| 2004/0213819 | A1 | 10/2004 | Albrecht |
| 2005/0013833 | A1 | 1/2005 | Simonnet |
| 2005/0112188 | A1 | 5/2005 | Eliaz et al. |
| 2005/0244342 | A1 | 11/2005 | Friedman et al. |
| 2006/0029657 | A1 | 2/2006 | Popp et al. |
| 2006/0115440 | A1 | 6/2006 | Arata et al. |
| 2008/0206317 | A1 | 8/2008 | Johnsson et al. |
| 2008/0274172 | A1 | 11/2008 | Moscoso et al. |
| 2012/0164214 | A1 | 6/2012 | Machluf et al. |
| 2014/0065260 | A1 | 3/2014 | Nakazawa et al. |
| 2014/0178320 | A1 | 6/2014 | Perruna et al. |

FOREIGN PATENT DOCUMENTS

| | | |
|---|---|---|
| CN | 1852701 A | 10/2006 |
| EP | 0956851 A1 | 11/1999 |
| EP | 1352639 A1 | 10/2003 |
| FR | 2802805 A1 | 6/2001 |
| FR | 2825629 A1 | 12/2002 |
| JP | 51-012591 B1 | 4/1976 |
| JP | 56-046810 B | 11/1981 |
| JP | 2004-331610 A | 11/2004 |
| JP | 2007-008853 A | 1/2007 |
| WO | 94/09829 A1 | 5/1994 |

(Continued)

OTHER PUBLICATIONS

Abram et al., "Mousses," Handbook of Cosmetic Science and Technology, (Barel, A.O.; Paye, Marc; Maibach, Howard I.) p. 221-232 (2001).
Anitra C. Carr, "Tee Trees and Their Therapeutic Properties", The Linus Pauling Institute, Fall/Winter 1998.
Brandl et al., "Morphology of semisolid aqueous phosphatidylcholine dispersions, a freeze fracture electron microscopy study," Chemistry and Physics of Lipids, 87, pp. 65-72 (1997).
Brandl et al., "Preparation and characterization of semi-solid phospholipid dispersions and dilutions thereof," International Journal of Pharmaceutics, 170, pp. 187-199 (1998).
Brandl et al., "Three-dimensional liposome networks: freeze fracture electron microscopical evaluation of their structure and in vitro analysis of release of hydrophilic markers," Advanced Drug Delivery Reviews 24, pp. 161-164 (1997).

(Continued)

*Primary Examiner* — Shirley V Gembeh
(74) *Attorney, Agent, or Firm* — Kaplan Breyer Schwarz LLP

(57) ABSTRACT

The invention relates to a foam formulation comprising an emulsion, comprising an oil phase and a water phase, the oil phase comprising at least one membrane-forming substance forming a lamellar membrane in the foam formulation.

10 Claims, 3 Drawing Sheets

(56)          References Cited

FOREIGN PATENT DOCUMENTS

| WO | 96/27376 A1 | 9/1996 |
| WO | 98/56333 A1 | 12/1998 |
| WO | 00/15193 A1 | 3/2000 |
| WO | 01/62222 A2 | 8/2001 |
| WO | 03/17968 A2 | 3/2003 |
| WO | 2005/027774 A2 | 3/2005 |
| WO | 2005/097069 A1 | 10/2005 |
| WO | 2006/110555 A2 | 10/2006 |
| WO | 2008/086953 A1 | 7/2008 |

OTHER PUBLICATIONS

Brandl, "Liposomes as drug carriers: a technological approach," Biotechnology Annual Review, vol. 7, pp. 59-85 (2001).

Caprylic Acid + Caprinic Acid, F&M Chemicals.

Caprylic acid—Compound Summary, National Center for Biotechnology Information PubChem Compound Database, http://pubchem.ncbi.nlm.nih.gov/summary/summary.cgi?cid=379&loc=ec_rcs, downloaded on Sep. 24, 2012.

Caprylic acid—Compound Summary; PubChem Compound Database, Sep. 16, 2004.

Daniels, "Manufacturing protocol for reworking Example 1 of US 2006-0029657," Apr. 10, 2013 (5 pgs.).

Decanoic acid—Compound Summary, National Center for Biotechnology Information PubChem Compound Database, http://pubchem.ncbi.nlm.nih.gov/summary/summary.cqi?cid=2969, downloaded Sep. 24, 2012 (10 pgs.).

Dissertation thesis of Inken Stoye, 1997, with partial translation.

EmulsiFlex-C3 Datasheet, Avestin Europe GmbH (1 page—undated).

Glombitza et al., "Influence of different ceramides on the structure of in vitro model lipid system of the stratum corneum lipid matrix," Chemistry and Physics of Lipids, 117, pp. 29-44 (2002).

Heike P. Schuchmann et al., Chemie Ingenieur Technik 2004, 76, No. 4, "Emulgieren: Mehr als nur Zerkleinern", 12 pages with English Abstract.

Heike P. Schuchmann, KIT, Lebensmittelverfahrenstechnik, Hochschulkurs Emulgiertechnik 2012, "Tropfenaufbruch beim mechanischen Emulgieren" together with an English translation of abstracts and slides.

Hydrogenated lecithin, from Environmental Working Group's Skin Deep® Cosmetics Database, downloaded on Jul. 16, 2012 (www.ewg.org).

Hydrogenated Lecithin, Skin Deep Cosmetics Database, 2012.

J. Wohlrab et al., "Interaction of Epicutaneously Applied Lipids with Stratum Corneum Depends on the Presence of either Emulsifiers or Hydrogenated Phosphatidylcholine", Skin Pharmacol Physiol 2010; 23; pp. 298-305.

JP 2004-331610, 2004, Machine Translation, 11 pages.

Klein, "Choosing Thickening Agents for Emulsions, Part I: Water Phase Thickeners," Cosmetics & Toiletries, vol. 118, No. 2, pp. 42-46 (2003).

Lecithin—The importance of phospholipid terminology, Inform, vol. 7, No. 11 (Nov. 1996), p. 1168.

Lecithin, Skin Deep Cosmetics Database, 2012.

Mehnert et al., "Solid lipid nanoparticles: Production, characterization and applications," Advanced Delivery Reviews 47, pp. 165-196 (2001).

Mintel GNPD, URL, http://www.gnpd.com/sinatra/gnpd/search_results&search_id=Wt6LtadEma/&p_page_number=2&item_id=140346.

Muller-Goymann, Photographs "TEM-Aufnahme und Polarisationsmikroskopie einer Lamellarphase," Pharmazeutische Technologie (2013) 1 pg.

Multi-Lamellar Emulsion, Wikipedia, hllp:/en.wikipedia.org/w/index.php?title"'Multi-Larnellar Emulsion&priniable-yes Last updated: Nov. 4, 2011; downloaded Sep. 4, 2014 (2 pgs.).

Multi-Lamellar Emulsion, Wikipedia, http:/en.wikipedia.org/w/index.php?title"'Multi-Larnellar Emulsion&priniable-yes Last updated: Nov. 4, 2011; downloaded Sep. 4, 2014 (2 pgs.).

New, "Antileishmanial activity of amphotericin and other antifungal agents entrapped in liposomes," J. Antimicrob. Chemother. 8:371-381, Oxford University Press, London, England (1981).

Pentylene Glycol, from Environmental Working Group's Skin Deep® Cosmetics Database, downloaded on Jul. 16, 2012 (www.ewg.org).

Pentylene Glycol, Skin Deep Cosmetics Database, 2012.

Photoseries regarding experiments concerning foam stability of WO 2008/155489 (9 pages—undated).

Prof. R. Daniels/Koko Firmenseminer, Mar. 3, 2012: "Lamellare System—ein Uberblick", 15 pages, with Translation.

Propylene Glycol, from Environmental Working Group's Skin Deep® Cosmetics Database, downloaded on Jul. 16, 2012 (www.ewg.org).

Schneider, "Lecithine—Gewinnung, Eigenschaften und Bedeutung fur die industrielle Anwendung", Fat Sci Technol., vol. 94, pp. 524-533 (1992).

Scholfield, "Composition of Soybean Lecithin", Journal of the American Oil Chemists' Society, vol. 58, No. 10, pp. 889-892 (1981).

Shah et al., "Interaction of Calcium Ions with Lecithin and Sphingomyelin Monolayers," Lipids 2(1):21-27, American Oil Chemists' Society, Springer, Germany (1967).

Shchipunov et al.: "Phase Behavior of Lecithin at the Oil/Water Interface", Langmuir, vol. 12, No. 26, pp. 6443-6445 (1996).

Steifel® Research Australia, "Physiogel foam investigation II," 5 pg. (Mar. 27, 2014).

Test Report Regarding Foam Stability; EP 2 020 221; 13 pgs.

Universal base creams with membrane structure for skin care, skin protection and dermatics published in Osterreichische Apothekerzeitun 56 (14), 679 (2002), p. 1-2.

US Pharmacopeia, pp. 3359-3360 (2006).

Usnea, Wikipedia, http://en.wikipedia.orgiw/index.php?title=Usnea&oldid=625407500,last updated: Sep. 13, 2014 (5 pages).

Wikipedia Extract—Information on Equisetum, Oct. 21, 2014, 4 pages.

WPI (World Patent Index) Accession No. 2004-826805 language abstract for JP 2004-331610 A, published Nov. 25, 2004, Derwent, Thomsom Reuters, New York, NY.

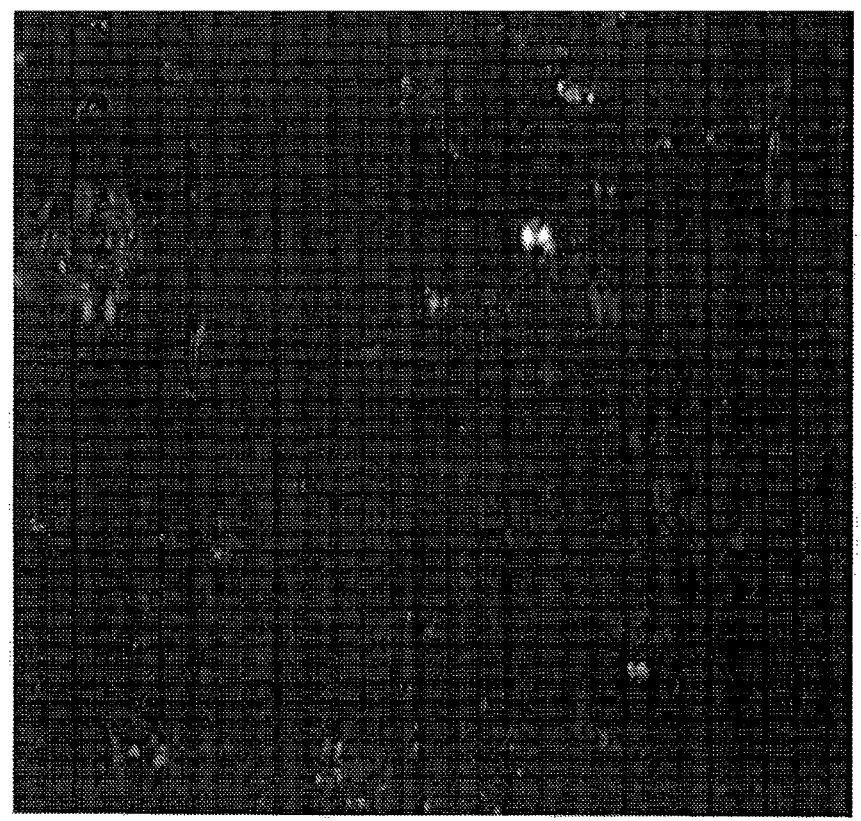
Figure 1: Polarization microscopic photograph of the phospholipid/water dispersion. Lamellar membrane-forming structures are shown as Maltese crosses.

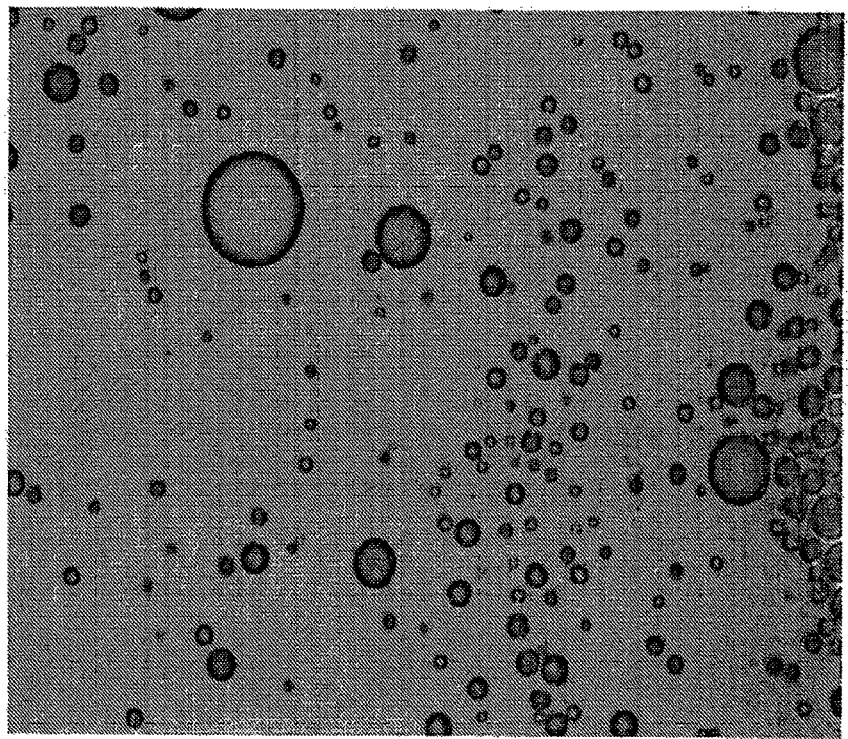
Figure 2: Polarization microscopic photograph of the foam cream. Lamellar membrane-forming structures are shown as Maltese crosses on the boundary surface of the gas bubbles of the foam (e.g. upper left area).

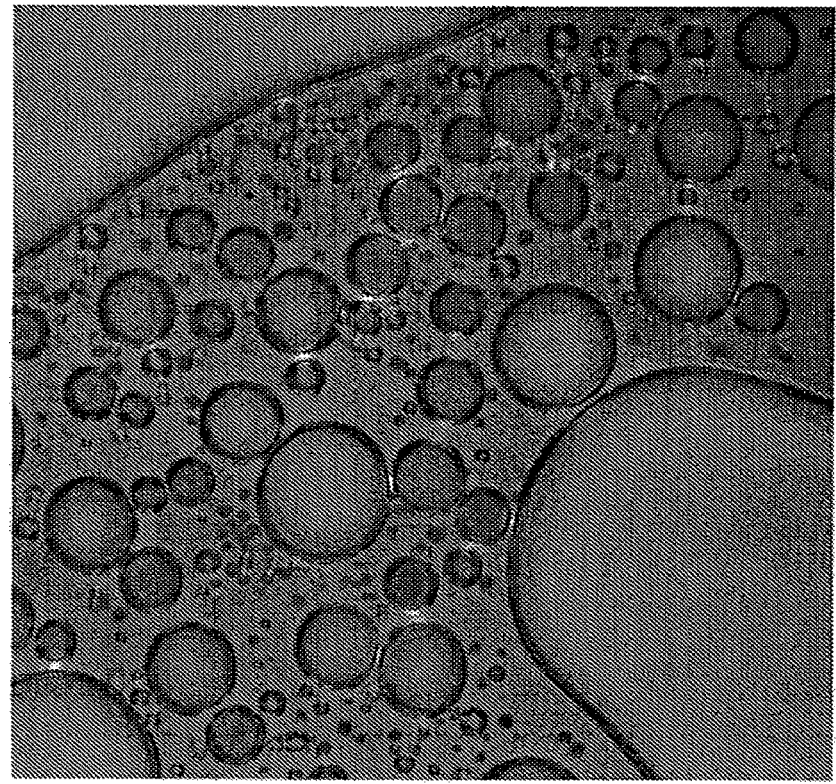
Figure 3: Polarization microscopic photograph of the foam cream. Lamellar membrane-forming structures are shown as Maltese crosses at the boundary surface of the gas bubbles of the foam.

DMS (DERMA MEMBRANE STRUCTURE) IN FOAM CREAMS

TECHNICAL FIELD OF THE INVENTION

The present invention relates to cosmetic and dermatologic foam formulations, particularly foam creams, based on emulsions of especially the oil-in-water type, wherein the oil phase comprises at least one membrane-forming substance forming a lamellar membrane in the foam formulation.

BACKGROUND OF THE INVENTION

1. Emulsions

The term "emulsion" generally relates to heterogeneous systems consisting of two liquids that are not miscible or are only miscible to a limited extent which are typically designated as phases. In an emulsion, one of both liquids is dispersed in the other liquid in the form of fine droplets.

In case that the two liquids are water and oil and the oil droplets are finely dispersed in water, the emulsion is an oil-in-water emulsion (O/W emulsion, e.g. milk). The basic character of an O/W emulsion is defined by the water. In case of a water-in-oil emulsion (W/O emulsion, e.g. butter), the opposite principle applies wherein the basic character is here defined by the oil. In order to obtain a durable dispersion of a liquid in another liquid, emulsions in a conventional sense require the addition of a surface active agent (emulsifier). Emulsifiers have an amphiphilic molecular structure consisting of a polar (hydrophilic) and a non-polar (lipophilic) part of the molecule which are separated from each other in space. In simple emulsions, finely dispersed droplets enclosed by an emulsifier shell of the one phase are present in the second phase (water droplets in W/O or lipid vesicles in O/W emulsions). Emulsifiers reduce the surface tension between the phases because they are arranged in the boundary surface between the two liquids. They form surface films at the boundary of the oil/water phases which countervails an irreversible joining of the droplets. For stabilizing emulsions mixtures of emulsifiers are often used.

Conventional emulsifiers can be classified depending on their hydrophilic part of the molecule into ionic (anionic, cationic and amphoteric) and non-ionic ones:

The best known example of an anionic emulsifier is believed to be soap which is the conventional name for the water-soluble sodium or potassium salts of saturated and non-saturated higher fatty acids.

Important members of cationic emulsifiers are the quaternary ammonium compounds.

The hydrophilic part of the molecule of non-ionic emulsifiers often consists of glycerol, polyglycerol, sorbitanes, carbohydrates or polyoxyethylene glycols, respectively, and is most often connected to the lipophilic part of the molecule by means of ester and ether bonds. The latter consists typically of fatty alcohols, fatty acids or iso-fatty acids.

The term "emulsifier" or "conventional emulsifier" respectively, is known in the art. Conventional emulsifiers are described, e.g., in the publications: Pflegekosmetik, 4th edition, Wissenschaftliche Verlagsgesellschaft mbH Stuttgart, pages 151 to 159 and Fiedler Lexikon der Hilfsstoffe, 5th edition, Editio Cantor Verlag, Aulendorf, pages 97 to 121.

By variation of the structure and the size of the polar and the non-polar part of the molecule, lipophilicity and hydrophilicity of emulsifiers can be modified to a large extent.

The correct choice of emulsifiers is decisive for the stability of an emulsion. In this respect, the characteristics of all compounds contained in the system need to be considered. For example, in case of skin care emulsions, polar oil components such as e.g. UV filters may lead to instabilities. Apart from emulsifiers, other stabilizers are, therefore, additionally used, which, e.g., increase the viscosity of the emulsion and/or act as protective colloid.

Emulsions represent an important type of product in the field of cosmetic and/or dermatologic preparations which is used in different application fields. Therefore, a variety of products—such as lotions and creams—are available for skin care, especially for relubricating dry skin. The aim of skin care is to compensate for the loss of lipid and water caused by daily washing. In addition, such skin care products should protect from environmental stress—in particular from sun and wind, and should delay skin ageing.

Cosmetic emulsions are also used as deodorants. Such formulations are used for eliminating the adore of the body that is formed when fresh sweat that as such is free of odour is decomposed by microorganisms.

Emulsions in the form of cleaning emulsions are also used for cleaning of the skin and skin adnexa. They are most often used for the cleaning of the face and especially for removing decorative cosmetic. Such cleaning emulsions have the advantage—in contrast to other cleaning preparations such as soap—to be especially mild on skin since they may contain in the lipophilic phase nurturing oils and/or non-polar active agents—such as, e.g., vitamin E.

Since decades, conventional emulsifiers form the basis for the development of skin care preparations. Emulsifiers were used as adjuvants for the manufacture and especially for stabilizing emulsions. Recently there were references that the use of emulsifiers in skin care preparations may lead to problems e.g. in case of sensitive skin since emulsifiers typically disturb the integrity of the natural skin barrier and, thus, cleaning of the skin may lead to a loss of natural barrier compounds of the skin. The loss of natural barrier compounds may lead to an increased roughness, dry skin, cracking and wear eczema.

Furthermore, the use of emulsifiers normally results in the conversion of lamellar structures of the lipid barrier into vesicular structures such as e.g. micelles or mixed micelles. These vesicles "destroy" at least a part of the barrier layer of the skin, and, therefore, locally increase the permeability of the barrier layer membrane. Due to this opening of the barrier layer of the skin, the loss of water across the skin (TEWL) is at least temporarily increased and simultaneously the capacity of the skin to bind moisture is decreased. Continuous application of skin care preparations having conventional emulsifiers may even lead to failure of the skin to maintain its protecting function.

Emulsifier-free emulsions are a special form of an emulsion. These emulsions are free of emulsifiers in a narrower sense, i.e. free of amphiphilic compounds having a low molecular weight (molecular weight of <5000) that in suitable concentrations form micelles and/or other liquid crystalline aggregates. The IUPAC defines the term "emulsifier" as follows: Emulsifiers (i.e. conventional emulsifiers) are surface-active substances. They are preferably arranged in the boundary surface between oil phase and water phase and, therefore, reduce the surface tension. Even in low concentration, emulsifiers facilitate the formation of an emulsion. In addition, these substances may increase the stability of an emulsion in that they reduce the rate of aggregation and/or coalescence. According to an interdisciplinary consensus of pharmacists, dermatologists and other experts of the Society of Dermatopharmacy (http://www.dermotopics.de/german/
ausgabe_1_03_d/emulgatorfrei_1_2003_d.htm), a formula-
tion may be defined as "emulsifier-free" when it is stabilized
by means of surface active macromolecules (having a
molecular weight of over 5000) instead of emulsifiers in a
narrower sense (conventional emulsifiers).

For stabilizing pharmaceutical and cosmetic emulsions,
so-called true emulsifiers are predominantly used, i.e. con-
ventional emulsifiers in the sense of the present description
that according to their structure and their physical-chemical
behaviour belong to the class of tensides. They are charac-
terized in an amphiphilic structure and the capability for
micelle association. Compounds and mixtures thereof that
lead to the formation of a lamellar membrane in the sense of
the present invention instead of micelle association are,
however, not considered as conventional emulsifiers.
Examples for such compounds are e.g. phospholipids, such
as e.g. lecithins, sphingolipids, ceramides, cholesterol, fatty
alcohols, fatty acids as well as there mono- and/or diesters,
as well as sterols, etc., when they are dispersed under
specific conditions as described below. Such mixtures of
compounds may further contain triglycerides (not hydro-
philic and lipophilic), squalene (not hydrophilic and lipo-
philic), or squalane (not hydrophilic and lipophilic). Pre-
ferred examples for membrane-forming substances of the
present invention are phospholipids, sphingolipids, cer-
amides, cholesterol, fatty alcohols, fatty acids as well as
their mono- and/or diesters, and sterols. These compounds,
e.g. phospholipids, are not soluble in water in contrast to
typical emulsifiers especially tensides having a comparable
HLB-value of about 10. Normally, they form no micelles or
hexagonal liquid crystalline phases. Above the phase tran-
sition temperature, they spontaneously form in water exclu-
sively large multilamellar vesicles (LUV). Below the phase
transition temperature, they can be dispersed in water under
high energy input and form lamellar structures. The above-
mentioned phase transition temperature indicates in this
respect the temperature at which a gel-like phase is con-
verted into a liquid crystalline phase. Below the phase
transition temperature, a gel phase is present, above the
phase transition temperature, a liquid crystalline phase is
present. Phase transition temperatures vary depending on the
composition (saturated/non-saturated; short/long) and typi-
cally lie, for example, in case of phospholipids between 10°
C. and 70° C. For a given system, the phase transition
temperature can easily be determined by means of DSC.

Membrane-forming substances also typically contain
lipophilic and hydrophilic parts of the molecule. The capac-
ity of a membrane-forming substance to form lamellar
structures as opposed to micelles depends, however, in
particular on the optimal area and/or (boundary surface
carbon/water), the volume V and the critical chain length $l_c$
(Israelachvili, Jacob N.: "Intermolecular and Surface
Forces: With Applications to Colloidal and Biological Sys-
tems". $2^{nd}$ Edition Academic Press, London, UK, 1992).

Furthermore, it is in case necessary to select special
production conditions for a system to form lamellar struc-
tures. These conditions are described below regarding the
inventive systems in more detail. Although systems in which
micellar structures can be converted under suitable condi-
tions into lamellar structures are known in the art, there are,
however, also systems in which no phase transformation into
another phase such as e.g. a micellar, hexagonal phase, etc.
is possible. Still other systems allow under suitable condi-
tions for the formation of a lamellar phase, however, an
alteration of the concentration does not lead to the formation
of other mesophases.

Thus, lamellar structures form under well-defined condi-
tions and are not arbitrarily convertible by means of an
alteration of the concentration into other mesophases such as
e.g. micellar structures. In case of water-soluble tensides
(emulsifiers), micelles, hexagonal and lamellar liquid crys-
talline phases are formed depending on the tenside concen-
tration. In this case, it is possible that depending on the
concentration mixtures of different states (hexagonal and
lamellar) are present side by side in equilibrium. By con-
trast, membrane-forming substances of the present invention
are typically not soluble in water. In case of these lipids not
soluble in water, such as e.g. phospholipids, liposomal
structures are as a rule not present side by side of lamellar
structures but either the one structure is present or the other.

An example of emulsifier-free emulsions are Pickering
emulsions. Pickering emulsions are stabilized by means of
solids which the finely divided solid particles stabilize the
emulsion so that conventional emulsifiers may be substan-
tially omitted. In this respect, the solids accumulate in the
oil/water boundary surface in the form of a layer whereby
the joining of the dispersed phases is prevented. Solid
emulsifiers suitable for this purpose are particulate inorganic
or organic solids that are wettable by both lipophilic as well
as hydrophilic liquids. In Pickering emulsions, titanium
dioxide, tin oxide, silicon dioxide, $Fe_2O_3$, veegum, bentonit
or ethyl cellulose are preferably used as solids.

However, such solid emulsifiers may also lead to irrita-
tions or may even cause allergies in case of sensitive skin.

Cream bases are already used employing a variety of
natural or skin-like ingredients, respectively, promising a
better skin compatibility especially in case of sensitive skin.
In this respect, it has been shown that the use of skin-like
ingredients results in an improved skin care. Thus, in these
cream bases several components of natural skin lipids, such
as e.g. triglycerides are replaced by caprylic acid/caprinic
acid triglycerides (of plant origin), squalene is replaced by
squalane (or plant origin), ceramides are replaced by cer-
amide 3 (of yeast origin), cholesterol is replaced by phy-
tosterols (of plant origin) and phospholipids are replaced by
phospholipids (of plant origin).

In this concept, typical adjuvants such as fragrances,
colorants, comedogen lipids (e.g. mineral oils), preserva-
tives and critical emulsifiers are preferably omitted, since
these components potentially are sensitizing and may lead to
irritations of the skin.

These formulations are preferably prepared without con-
ventional emulsifiers in order to avoid the above-mentioned
disadvantages of conventional emulsifiers.

Without wishing to be bound by a specific theory it is
believed that the special action of these specifically com-
posed membrane lipids is related to the lamellar structure.
Omission of conventional emulsifiers prevents that micelles
or vesicles are formed so that the lamellar structure of the
formed membrane is maintained in the emulsion. This
lamellar structure is based on the (physical) structure and the
(chemical) composition of the natural epidermal skin lipids
that are preferably present as lute substance between the
cells (corneocytes) of the stratum corneum.

Systems based on specifically composed membrane lipids
having a lamellar structure of the membrane are known in
the art under the term "DMS®" (Derma Membrane Struc-
ture).

3. Foam Formulations

A special application form of cosmetic and/or dermato-
logic emulsions is the application as foams. Foam formula-
tions have the advantage that they can easily be distributed
on the skin. The foamy consistency is experienced as comfortable and the products normally leave a good skin feeling. In particular, the physical structure of the foam acts positively on the protective action of the skin. Foams are complicated physical structures that require a special balance of the components constituting the foam. In general, foams are obtained by spraying a formulation of an emulsion or an aqueous tenside (stabilizer) solution. For example, an emulsion containing propellant is dispensed from a pressurized container (such systems are also described in literature and patent literature as aerosol foams). In this case, the pressurized mixture of emulsion and propellant expands and forms small foam bubbles. In particular, the dispersed oil phase in which the oil-soluble gas is dissolved expands. However, foams can also be formed by means of other systems such as, for example, pump sprays.

Upon application, balanced foam formulations have a stable polydisperse structure of two or more phases that forms on the skin a network structure that is comparable to a membrane. Such network structures have the advantage that they develop a protective action, for example against contact with water, however, allow for the unhindered gas exchange with the environment. In such foams, there is practically no obstacle for the perspiratio insensibiles and no corresponding heat build-up. Thus, the positive properties of a protective and nurturing action is combined with an unchanged perspiration.

Foam formulations known so far contain conventional tenside/emulsifiers that serve for the stabilization of the emulsion and for the resulting foam stability.

Conventional emulsifiers or tensides, respectively, are, however, repeatedly identified as causing irritations in the use of skin care products, such as e.g. a dysfunction of the skin barrier or Mallorca acne.

Thus, there is a need of individual skin care compositions that are better adapted to the needs of the skin than conventional emulsion systems on the basis of emulsifiers and, thus, provide a better skin protection and a better skin care.

The use of cream bases having a lamellar structure based in its composition on the membrane-forming epidermal lipids in foam formulations so far has not been described.

It is the object of the present invention to provide improved foam formulations, particularly improved foam creams, avoiding the above-mentioned disadvantages of formulations according to the state-of-the-art.

SUMMARY OF THE INVENTION

The applicant has surprisingly found that emulsions comprising an oil phase and a water phase wherein the oil phase comprises at least one membrane-forming substance forming a lamellar membrane in the foam formulation are suitable as basis for foam formulations. In a preferred embodiment, the foam formulations are substantially free of emulsifier, i.e. they substantially contain no conventional emulsifiers wherein the substance or the mixture of substances that leads to the formation of a lamellar membrane is not considered a conventional emulsifier. For example, in the technical field it is, for example, acknowledged to characterize the commercial product Physiogel® cream containing DMS® concentrate as "emulsifier-free".

Membrane-forming substances and mixtures of substances according to the present invention are typically non-soluble in water, while conventional emulsifiers, especially tensides having a comparable HLB-value of about 10 are as a rule soluble in water. Furthermore, the membrane-forming substances not soluble in water according to the present invention are not capable of spontaneously emulsifying oils, while conventional emulsifiers especially those having a high HLB-value are capable to spontaneously emulsify oils. Conventional emulsifiers having a low HLB-value are not capable to form lamellar structures or liposomes alone in contrast to membrane-forming substances according to the present invention, e.g. phospholipids. A special feature of membrane-forming substances according to the present invention in contrast to conventional emulsifiers is that, for example, phospholipids have a HLB of 10, however, are not soluble in water.

Preferably the membrane-forming substances of the invention have a HLB-value of more than 8, more preferably of 9 to 11, and most preferably of 9.5 to 10.5.

According to the present invention the positive characteristics of foam formulations are combined with those of emulsions in which the oil phase comprises at least one membrane-forming substance that forms a lamellar membrane in the foam formulation. Thus, especially foam formulations can be prepared combining the positive properties of the foam, namely the physical structure and the convenient application, with a good skin compatibility. This property allows the use of foam formulations for cosmetic and dermatologic formulations to be employed in case of sensitive types of skin. Thus, skin compatibility and convenience of application is combined advantageously with each other. The lamellar structure of the at least one membrane-forming substance that is important for the skin compatibility has not been considered in foam formulations of the state-of-the-art.

Nevertheless, it is not obligatory that such emulsions lead to stable foam products upon foaming. Foams are obtained, as already mentioned, e.g. by incorporating propellants into O/W emulsion systems. In case that the propellant dissolved in the dispersed oil phase evaporates upon foaming, a foam is foamed (dispersion of gas in liquid). Foaming or expanding, respectively, of the propellant dissolved in the dispersed oil phase leads to a dilatation of the dispersed oil phase. It now has been surprisingly found that upon foaming of the inventive foam formulations breaking of the preparation does not occur and a suitable foam is formed. The formed foam is stable enough in order to be, e.g., applied to the skin.

The invention relates to foam formulations comprising an oil phase and a water phase, wherein the oil phase comprises at least one membrane-forming substance that forms a lamellar membrane in the foam formulation.

Preferably, the invention relates to foam formulations on the basis of natural or skin-like ingredients, respectively, providing for a better skin compatibility.

Furthermore, the invention relates to the use of foam formulations based on emulsions as carriers for active agents, as skin care agent, as skin cleaning agent or as sunscreen. The foam formulation, therefore, can be employed as cosmetic, medical product or pharmaceutical composition.

Moreover, the invention comprises a method of manufacture of foam formulations based on emulsions in which the oil phase comprises a membrane-forming substance that forms a lamellar membrane in the foam formulation. The method comprises the steps:

a) Producing an emulsion preferably of the oil-in-water type, b) Filling the emulsion and propellant into a pressurized container, or c) Filling the emulsion into a container other than a pressurized container that upon dispensing of the emulsion generates a foam.

DESCRIPTION OF THE DRAWINGS

FIGS. 1-3 show polarization microscopic photographs of the foam formulation of example 3.

FIG. 1 shows lamellar membrane-forming structures that can be recognized by means of the so-called Maltese crosses (especially in the upper left image area).

In addition, in FIG. 2, the gas phase of the foam formulation can be recognized in the form of gas bubbles. Maltese crosses can be shown especially in the boundary surface to the gas phase.

Moreover, in FIG. 3, Maltese crosses can be recognized in the boundary surface to the gas bubbles of the foam.

DETAILED DESCRIPTION OF THE INVENTION

According to the present invention, foam formulations are formulations, especially emulsions, that are evidently adapted for the formation of a foam. In particular, the formulations may be either filled together with a propellant into a pressurized container or may be filled without propellant into a container other than a pressurized container that allows for the formation of a foam upon dispensing of the formulation/emulsion. For example, pump spray containers may be used.

In a preferred embodiment, the foam formulation is a foam cream.

According to the present invention, essentially emulsifier-free emulsions are such emulsions that do not contain more than 1.5 weight percent of conventional emulsifiers, preferably not more than 1.0%, more preferably not more than 0.5%. According to the invention, emulsifier-free emulsions are such emulsions that do not contain conventional emulsifiers.

According to the present invention, a membrane-forming substance forming a lamellar membrane is a substance that preferably has simultaneously a hydrophilic as well as a hydrophobic part of the molecule. Preferred are substances such as e.g. phospholipids, such as lecithins, sphingolipids, ceramides, cholesterol, fatty alcohols, fatty acids as well as mono- and/or diesters thereof, as well as sterols, etc. Triglycerides (not hydrophilic and lipophilic), squalene (not hydrophilic and lipophilic), squalane (not hydrophilic and lipophilic), may also be contained in mixtures of compounds comprising the membrane-forming substance. Preferred membrane-forming substances are phospholipids, sphingolipids, ceramides, cholesterol, fatty alcohols, fatty acids as well as their mono- and/or diesters, and sterols. Such substances or corresponding mixtures of substances can be dispersed in a suitable way with an aqueous phase under formation of lamellar membranes. This can be achieved, for example, by dispersing under high energy input (e.g. high pressure homogenization, ultrasound). In case of high pressure homogenization, pressures in the range of 50.000-250.000 kilopascal (500-2500 bar) are employed in this respect, more preferably of 100.000-150.000 kilopascal (1000-1500 bar). In other cases, a high energy input for forming lamellar membrane structures is not compulsory necessary (for example often in case of using non-hydrogenated lecithins having a low phase transition temperature in connection with suitable lipids, such as e.g. isopropyl myristate). The use of particular concentrates forming a lamellar phase is also possible.

The presence of lamellar structures in the dispersion can easily be determined by a person skilled in the art by means of methods known in the art. Suitable methods of measuring are, for example, described in Claus-Dieter Herzfeld et al. (editor), Grundlagen der Arzneiformlehre, Galenik 2, Springer Verlag, 1999. In this respect, the method of polarization microscopy is especially worth noticing. In this method, two polarization films in the so-called cross position in which the oscillation planes of the generated polarized light are perpendicular to each other are placed above and below the object to be analyzed. The oscillation plane of the irradiated light is changed by the sample so that a fraction of the light can pass through the second polarization film. The presence of lamellar phases can be recognized here typically by means of so-called Maltese crosses.

According to the present invention, a lamellar membrane is arranged such that it has a layered structure such that the upper layer of the substance is respectively directed to a lower layer of the substance. The direction of the individual substance layers occurs independently of the used solvent such that e.g. the hydrophilic parts of the substance are directed outwards and the hydrophobic moieties are directed inwards to each other, or vice versa.

In case that two layers of the substance are directed in the above-described sense, the resulting structure is designated as a single membrane, while in case of arranging two further layers, this lamellar structure is designated as a double membrane. According to the present principle, still further layers may be associated to the (double) membrane already present resulting in a multiple membrane structure. According to the present invention, the membrane may be present as a single membrane, as a double membrane or also as a multiple membrane.

A "wash-out" effect is understood as a decreasing of the moisture of the skin after completing an application of the skin care composition below the initial value.

According to the present invention, bioidentical fats are fats of plant origin that occur in the body.

Oil Phase

Suitable components that may form the oil phase may be selected from polar and unpolar lipids or mixtures thereof.

The oil phase of the inventive formulations is advantageously selected from the group of phospholipids, such as lecithins, (mono-, di-, tri-) glycerides (especially triglycerides, such as e.g. fatty acid triglycerides), sphingolipids, from the group of propylene glycol or butylene glycol fatty acid esters, from the group of natural waxes of animal or plant origin, from the group of ester oils, from the group of dialkyl ethers and dialkyl carbonates, from the group of branched and non-branched hydrocarbons and waxes as well as from the group of cyclic and linear silicon oils.

Foam formulations according to the present invention allow for an improved skin care action of the formulation due to the lamellar membrane structure and the resulting structural similarity to the structure of intercellular lamellar lipid structure of epidermal lipids, especially the stratum corneum. Due to the analogous structure of the lamellar structure of the skin, integration of the membrane into the skin is facilitated. The integration leads also to an improvement, especially a stabilization and recovery of the skin barrier. An intact skin barrier protects the skin from too high a moisture loss. An improvement of the skin barrier can also result in an improved smoothing of the skin and may decrease the "wash-out" effect, whereby advantageously an improved long-term effect is obtained in comparison to conventional foam formulations.

Preferred foam formulations of the present invention employ "skin-like" components, in order to obtain similarity of the lamellar membrane present in the foam formulation with the skin. In this respect, especially preferred embodiments replace, e.g., the natural glycerides present in the sub-corneas layer (the skin predominantly contains a mixture of di- and triglycerides) by, e.g., triglycerides (of plant origin), squalane by, e.g. squalane, which is less sensitive to oxidation, ceramides by ceramide 3 (from yeast), cholesterol by phytosteroles (of plant origin) and phospholipids by phospholipids (of plant origin).

In a preferred foam formulation of the invention, the membrane-forming substance comprises a lipid, more preferably a triglyceride and/or phospholipid. In an especially preferred foam formulation of the invention, the triglyceride is caprylic acid/caprinic acid triglyceride and/or the phospholipid is hydrogenated lecithin.

In a further preferred foam formulation of the present invention, the formulation may further comprise lecithin, preferably hydrogenated lecithin.

The preferred inventive foam formulations may further contain further components, such as e.g. stabilizers such as e.g. alcohols or glycols. Preferred are glycols, in particular propylene glycol, caprylyl glycol or mixtures thereof.

In preferred foam formulations of the invention, further components may be comprised such as e.g. *Butyrospermum parkii* (shea butter), squalane, glycerides, ceramides, preferably ceramide 3, or mixtures thereof.

A preferred foam formulation of the invention comprises a substantially emulsifier-free emulsion. An especially preferred foam formulation of the invention is free of emulsifier. In a particularly preferred embodiment, the foam formulation is free from water-soluble conventional emulsifiers having a HLB-value of about 10. In a preferred embodiment, the formulation is especially free from the following compounds:

Carboxylates, such as e.g. sodium stearate, aluminium stearate;

sulphates, such as e.g. Na-dodecyl sulphate, Na-cetyl stearyl sulphate, Na-laurylether sulphate;

Sulphonate: Na-dioctylsulphosuccinate;

Quaternary ammonium compounds, such as e.g. cetyl trimethyl ammonium bromide, benzalconium bromide;

Pyridinium compounds, such as e.g. cetyl pyridinium chloride;

Betains, such as e.g. betain monohydrate;

Macrogol fatty acid esters, such as e.g. macrogol-30-stearat;

Glycerol fatty acid esters, such as e.g. glycerol monostearate, glycerol monooleat, glycerol monoisostearate, partial glycerides, polyoxyethylene sorbitan fatty esters of medium chain length, such as e.g. Tween®, polyoxyethylene-(20)-sorbitan monostearat;

Sorbitan fatty acid esters, such as e.g. sorbitan laurat, sorbitan monooleat, sorbitan monopalmitate, sorbitan monostearate, sorbitan tristearate, sorbitan sesquioleat;

Sucrose fatty acid esters, such as e.g. sucrose monostearate, sucrose distearate, sucrose cocoate;

Macrogol fatty alcohol ethers, such as e.g. Cetomacrogol 1000, macrogol cetostearylether, macrogol oleylether, Lauromacrogol 400;

Stearin alcohols, such as e.g. cholesterol, lanolin, acetylated lanolin, hydrogenated lanolin, lanolin alcohols;

macrogol glycerol fatty acid esters, such as e.g. macrogol-1000-glycerol-monooleat, Macrogol-1000-glycerol-monostearat, macrogol-1500-glycerol, triricinoleat, macrogol-300-glycerol-(hydroxyl stearat), macrogol-5-glycerol-stearat, macrogol glycerol hydroxystearat;

Polyglyercol fatty acid ester, such as e.g. triglycerol diisostearat.

In the present invention, the oil phase comprising a suitable substance or such a mixture of substances for forming the lamellar membrane is dispersed with a water phase under conditions that result in the formation of a lamellar phase. If necessary, this is done, for example, by dispersing under high energy input, such as e.g. by ultrasound or by means of high pressure homogenization, wherein pressures of about 50.000 to about 250.000 kilopascal (about 500 to about 2500 bar), preferably about 100.000 to about 150.000 kilopascal (about 1000 to about 1500 bar) are used. In other cases, especially when using non-hydrogenated lecithin having a low phase transition temperature as the membrane-forming substance, simple dispersing is often already sufficient without the additional need of high energy input. The presence of a lamellar phase can, as mentioned above, easily be determined by a person skilled in the art using methods known in the art such as e.g. polarization microscopy.

In an especially preferred embodiment, the membrane-forming substance comprises a phospholipid, such as e.g. lecithin or hydrogenated lecithin, and additionally a lipid. More preferably, the phospholipid is a mixture of lecithin and hydrogenated lecithin. In an especially preferred embodiment, the weight ratio of lecithin to hydrogenated lecithin is about 10:1 to about 1:10, more preferably about 5:1 to about 1:5 and still more preferably the ratio of lecithin to hydrogenated lecithin is about 1:1. The lipid present in addition to phospholipid comprises in a preferred embodiment a liquid wax ester, such as e.g. isopropyl myristate, -palmitat, stearat or the like. Furthermore, further optional lipids, such as e.g. peanut oil or triglycerides of medium chain length (preferably $C_8$-$C_{12}$ triglycerides), may be present in addition to wax ester. The weight ratio of total phospholipid (e.g. lecithin+hydrogenated lecithin) to total lipid (e.g. wax ester+optional triglycerides) is in this embodiment preferably about 1:5 to about 1:1, preferably about 1:2.

The mixture of phospholipid and lipid is, for example, dispersed as a melt with water under high energy input. The high energy input can be effected by means of ultrasound or by means of high pressure homogenization, wherein pressures of 50.000 to 250.000 kilopascal (500 to 2500 bar) are employed, preferably 100.000 to 150.000 kilopascal (1000 to 1500 bar). In the water phase, further additives may optionally be present as described in the present specification, such as e.g. glycerol or thickening agent (e.g. xanthan gum and/or hydroxypropylmethyl cellulose (hypromellose)).

Further optional ingredients are described below in connection with DMS® compositions. In particular, the obtained formulation may be substantially emulsifier-free, preferably free of emulsifier, i.e. in the formulation, substantially no or no, respectively, conventional emulsifier is present, wherein the membrane-forming substance or the membrane-forming mixture of substances is not considered a conventional emulsifier. Upon dispersing this mixture in the described manner, a dispersion is obtained that is suitable for forming a foam formulation (e.g. by using propellants or a pump spray) and further for forming a lamellar membrane.

Further cream bases based on the above-described "skin-like" components are also known in the art as DMS® cream bases.

The DMS® base compositions can have the following components: caprylic acid/caprinic acid triglyceride, shea butter, squalane, ceramide 3, hydrogenated lecithin, palm glycerides, *Persea gratissima*, palm oil (*Elaesis guineensis*).

As stabilizers in the DMS® compositions may be used e.g. alcohols or glycols such as e.g. pentylene glyclol, caprylyl glycol or mixtures thereof.

A commercially obtainable DMS® base comprises caprylic acid/caprinic acid triglyceride, shea butter, squalane, ceramide 3, hydrogenated lecithin as well as pentylene glycol.

A further commercially obtainable DMS® base comprises caprylic acid/caprinic acid triglyceride, shea butter, squalane, ceramide 3, hydrogenated lecithin as well as alcohol.

A further commercially available DMS® base comprises caprylic acid/caprinic acid triglyceride, shea butter, squalane, ceramide 3, hydrogenated lecithin, *Persea gratissima* as well as caprylyl glycol.

A further commercially available DMS® base comprises caprylic acid/caprinic acid triglyceride, shea butter, squalane, ceramide 3, hydrogenated lecithin, palm glycerides, *Elaesis guineensis* as well as pentylene glycol.

A preferred DMS® base comprises caprylic acid/caprinic acid triglyceride, *Butyrospermum parkii*, squalane, ceramide 3, hydrogenated lecithin, as well as pentylene glycol.

An especially preferred caprylic acid/caprinic acid triglyceride is obtainable under the designation Miglyol 812 of the company Sasol and mixtures thereof with further oil and wax components.

In addition, especially preferred is the caprylic acid/caprinic acid triglyceride obtainable under the designation Miglyol 812 of the company Sasol/Myritol 312 of the company Cognis.

The inventive emulsions preferably contain from about 5 to 50 weight percent oil phase, especially preferably 10 to 35 weight percent and more preferably 15 to 35 weight percent oil phase. The data respectively refers to the total weight of the emulsion without propellant.

These cream compositions are in particular used in case of irritated, dry up to very dry, sensitive up to very sensitive, allergic and eczemic skin.

In addition, the oil phase preferably may contain further components, such as e.g. fatty acids, in particular stearinic acid, or oils, such as e.g. Cetiol V.

In the DMS concentrates and the inventive formulations, further conventional adjuvants (not bioidentical) such as fragrances, colorants, comedogene lipids (e.g. mineral oils) and physiologic emulsifiers are preferably omitted, since these components are potentially sensitizing and may lead to irritations of the skin.

Aqueous Phase:

The aqueous phase can contain cosmetic adjuvants, e.g. lower alcohols (e.g. ethanol, isopropanol), lower dioles or polyoles as well as ethers thereof (e.g. propylene glycol, glycerole, butylene glycol, hexylene glycol and ethylene glycol), foam stabilizers and thickening agents.

Suitable thickening agents are polymeric thickening agents that are partly soluble in water or are at least dispersible in water and form in aqueous systems gels or viscous solutions. They increase the viscosity of the water in that they either bind water molecules (hydratation) or, on the other hand, include and encapsulate the water into their intertwined macromolecules wherein movability of the water is decreased. Suitable polymers are:

- modified natural materials, such as cellulose ether (e.g. hydroxypropyl cellulose ether, hydroxyethyl cellulose and hydroxypropylmethyl cellulose ether);
- natural compounds, such as e.g. agar-agar, carrageen, polyoses, starch, dextrins, gelatine, casein;

- synthetic compounds, such as e.g. vinyl polymers, polyether, polyimines, polyamides and derivates of polyacrylic acid; and
- inorganic compounds, such as e.g. polysilicic acid and clay minerals.

Preferably, a cellulose ether is contained as thickening agent in the formulation of the invention. Hydroxypropylmethyl cellulose is especially preferred. A hydroxypropylmethyl cellulose especially preferred according to the invention is Metolose 90S H100. The general designation in the art for Hydroxypropylmethyl cellulose is hypromellose.

A further preferred thickening agent is xanthan gum, especially Keltrol® CG xanthan gum.

Hydroxypropylmethyl cellulose and xanthan gum can be employed in the inventive formulations also simultaneously.

The inventive emulsions preferably contain from 0.2 to 3.0 weight percent thickening agent (based on the dry weight of the thickening agent and the total weight of the emulsion without propellant). Especially preferred are 0.5 to 2.5 weight percent thickening agent.

Active Agents:

The contained active agent may be selected from all active agents and mixtures thereof that can be applied to the surface of the skin. The active agent can act cosmetically or pharmaceutically. Accordingly, cosmetic or dermatologic (to be employed as medical product or pharmaceutical composition) foam formulations are obtained. Furthermore, the formulation may be employed for protecting the skin against environmental influences. The active agent can be completely of plant origin or can be synthetic. The group of active agents may overlap with other groups of ingredients, such as e.g. the oil component, the thickening agents or the solid emulsifiers. For example, some oil components also may act as active agents, such as e.g. oils having polyunsaturated fatty acids or solid emulsifiers, such as e.g. particulate titanium dioxide that may serve as UV-filter. Depending on the characteristics, the substances are to be classified into several groups.

Active agents of the inventive formulations are advantageously selected from the group of substances having moisturizing and barrier strengthening properties, such as e.g. hydroviton, an emulation of NMF, pyrrolidone carbonic acid and salts thereof, lactic acid and salts thereof, glycerol, sorbitol, propylene glycol and urea, substances of the group of proteins and protein hydrolysates, such as e.g. collagen, elastin as well as silk protein, substances of the group of glycose aminoglucanes, such as e.g. hyaluronic acid, of the group of carbohydrates, such as e.g. pentavitin that corresponds in its composition to the carbohydrate mixture of the human sub-corneous layer and the group of lipids and lipid precursors such as for example ceramides. Further advantageous active agents in the sense of the present invention may be selected from the group of vitamins, such as e.g. panthenol, niacin, ax-tocopherol and its esters, vitamin A as well as vitamin C. Moreover, active agents selected from the group of antioxidants e.g. galates and polyphenoles may be used. Urea, hyaluronic acid and pentavitin are preferred substances.

It is further preferred that substances having skin soothing and regenerative action are employed as active agents, such as e.g. panthenol, bisabolol and phytosteroles.

Advantageous active agents in the sense of the present invention are also plants and plant extracts. These are e.g. algae, aloe, arnica, barber's rash, comfrey, birch, nettle, calendula, oak, ivy, witch hazel, henna, hop, camomile, ruscus, peppermint, marigold, rosemary, sage, green tea, tea tree, horsetail, thyme and walnut as well as extracts thereof.

The inventive formulations may further contain as active agents antimycotics and antiseptics/disinfectants of synthetic or natural origin.

Further active agents are glycocorticoides, antibiotics, analgetics, antiphlogistics, antirheumatics, antiallergics, antiparasitics, antipruriginosics, antipsoriatics, retinoids, local anaesthetics, therapeutic agents for veins, ceratolytics, hyperemic substances, coronary therapeutic agents (nitrates/nitro-compounds), virus statics, cytostatics, hormones, agents promoting wound healing, e.g. growth factors, enzyme preparations and insecticides.

Further Components of the Emulsion:

The formulations may optionally further contain colouring agents, pearlescent pigments, fragrances/perfumes, sunscreen filter substances, preservatives, complex formers, antioxidants and repellent agents, as well as pH-value regulating agents.

However, in a preferred embodiment, formulations of the invention are free from components that may lead to irritations of the skin, in particular are free from fragrances, perfume, colorants and conventional emulsifiers.

The inventive foam formulations may contain apart from the components already described above further natural fats such as e.g. shea butter, neutral oils, olive oil, squalane, ceramides and moisturizing substances as usual in the art.

The above list of individual components of the emulsion should be considered such that individual exemplified components may be classified into several groups because of its different properties.

Propellants:

Suitable propellants are e.g. $N_2O$, propane, butane and i-butane. The completed foam formulation contains 5 to 15 weight percent of propellant, preferably about 10 weight percent.

Method of Manufacture

The foam formulations according to the invention are prepared by providing an emulsion, preferably of the oil-in-water type and filling the emulsion and optionally propellant into a suitable container such as e.g. a pressurized container. As an alternative to propellant and pressurized container, the emulsion may also be filled into a different container that is suitable to dispense the emulsion as a foam even in the absence of propellant. Such systems are known to a person skilled in the art.

In particular, the inventive emulsions are prepared by means of a method comprising the following steps:

(1) Providing an oil phase optionally comprising at least one membrane-forming substance forming a lamellar membrane in the formulation, (2) Providing an aqueous phase, (3) Combining and homogenizing of both phases, for example, by means of ultrasound or high pressure homogenization, (4) Optionally adding at least one or at least one further membrane-forming substance, (5) Optionally homogenizing, for example, by means of ultrasound or high pressure homogenization in order to obtain an emulsion, wherein in at least one of the steps (1) or (4) at least one membrane-forming substance is included that forms in the formulation a lamellar membrane.

Preferably, the oil phase and the aqueous phase are each mixed at a temperature in the range of from about 40 to 90° C. and are homogenized; a temperature range of from about 60 to about 80° C. is especially preferred, more preferably a temperature of about 70° C.

For homogenizing, every means or method known in the art can be used. Preferably, the phases are homogenized using a high-speed stirring device. In a preferred embodiment, homogenizing is carried out by means of high pressure homogenization. In a further preferred embodiment, homogenizing is carried out by means of ultrasound.

In a preferred production method, the oil phase is mixed into the aqueous phase and is homogenized. If necessary, the emulsion is cooled down to room temperature under stirring. In an especially preferred method, a suitable amount of a DMS® concentrate is added to this mixture and the concentrate is incorporated into the present emulsion. The method that is described in the following can also be carried out with other lamellar phases instead of DMSO concentrate.

The DMS® concentrate can already be added to the oil phase before homogenizing with the aqueous phase or can be added to the mixture of the homogenizing the oil and aqueous phase. It is preferred that the DMS® concentrate is added to the mixture after the first homogenizing step and the mixture is then homogenized.

In case the emulsion comprises a thickening agent, the method advantageously comprises the following further steps:

(6) Providing an aqueous solution of thickening agent, (7) Mixing the solution of thickening agent with the emulsion.

Preferably, the inventive emulsion is loaded with about 10 weight percent of propellant.

Applications

The foam formulations of the present invention can be employed for all cosmetic and dermatologic (as a medical product or pharmaceutical composition) purposes. For example, the formulations may be employed as skin care agent or skin cleaning agent. Furthermore, they may be used as carriers for active agents and may be employed in the medical dermatologic field. In particular, the formulations may be employed as sunscreen.

EXAMPLES

Composition of the Foam Formulation a) Aqueous Phase

The aqueous phase is provided by mixing the components.

| Component | Amount |
|---|---|
| HPMC (Metolose 90SH100) | 1.5 g |
| Xanthan gum (Keltrol ® CG) | 0.5 g |
| Water | 78 g | b) Oil phase

Example 1

| Component | Example 1 |
|---|---|
| DMS Concentrate | 5 g |
| Miglyol 812 | 14 g |
| Stearinic acid | 1 g |
| Aqueous phase | ad 100 g |

US 12,685,697 B2

15

Example 2

| Component | Example 2 |
|---|---|
| DMS Concentrate | 5 g |
| Miglyol 812 | 14 g |
| Stearinic acid | 1 g |
| Cetiol V | 5 g |
| Aqueous phase | ad 100 g |

Stearinic acid is dissolved under heating up to about 70° C. in Miglyol 812 (Example 1) or in the mixture of Miglyol 812 and Cetiol V (Example 2), respectively.

This oil phase is added into the aqueous phase under stirring and is homogenized using a high-speed stirring device. The resulting emulsion is cooled down to room temperature under stirring and the DMS® concentrate is incorporated by means of a high-speed stirring device.

The used DMS® concentrate has the following INCI components:

Aqua (and) Hydrogenated Lecithin (and) Caprylic/Capric Triglyceride (and) Pentylene Glycol (and) *Butyrospermum parkii* (and) Glycerin (and) Squalanee (and) Ceramide 3

Manufacture of the Foam Formulation 90 g of the emulsion prepared as above are filled into an aerosol container and are loaded after closing with a valve cap with 10 g propellant.

Example 3

| Component | Example 3 |
|---|---|
| soya lecithin | 3.0 g |
| hydrogenated soya lecithin | 3.0 g |
| triglycerides of medium chain length | 7.0 g |
| isopropyl myristate | 7.0 g |
| xanthan gum | 0.4 g |
| hypromellose | 1.2 g |
| glycerol 85% | 5.0 g |
| water | 73.4 g |

Manufacture

The mixture of soya lecithin and hydrogenated soya lecithin (e.g. Phospholipon 80 H and phospholipon 85 G) is dissolved in a mixture of triglycerides of medium chain length (e.g. Miglyol 812) and isopropyl myristate at 60° C. Under high energy input (e.g. ultrasound or high pressure homogenization), the lipid melt is dispersed in a mixture of water and glycerol (high pressure homogenizer: Avestin Emulsiflex-C3; pressure: 1400 bar). Subsequently, the solution of xanthan gum (e.g. Keltrol CG) and hypromellose (e.g. Metolose 90SH100) in water is added under stirring.

Manufacture of the Foam Formulation 90 g of the membrane-forming emulsion as prepared above are filled into an aerosol container and is loaded with 10 g propellant after closing with a valve cap.

Foam Formation

A stable cream-like foam having fine bubbles is formed upon dispensing the foam formulation from the pressurized container by means of a suitable valve having a foam applicator attached. The structure of the cream-like foam is maintained for a duration that is sufficient for uniformly dispersing the foam on the skin.

The invention claimed is:

1. A foam formulation comprising an oil-in-water emulsion which comprises an oil phase and a water phase, wherein the oil phase comprises membrane-forming substances that form a lamellar membrane within the emulsion, said membrane-forming substances comprising at least one phospholipid and at least one lipid selected from the group consisting of a triglyceride and a liquid wax ester, wherein the formulation contains less than 1.5% by weight of amphiphilic, micelle-forming compounds having a molecular weight of less than 5000, and wherein said lamellar membrane is characterized by the presence of Maltese crosses when viewed under a polarization microscope.

2. The foam formulation of claim 1, wherein the at least one phospholipid is hydrogenated lecithin and the triglyceride is a caprylic/capric acid triglyceride.

3. The foam formulation of claim 1, wherein the at least one phospholipid comprises a mixture of lecithin and hydrogenated lecithin.

4. The foam formulation of claim 1, wherein the at least one lipid is a liquid wax ester comprising isopropyl myristate.

5. The foam formulation of claim 1, wherein the weight ratio of the at least one phospholipid to the at least one lipid is from 1:5 to 1:1.

6. The foam formulation of claim 1, further comprising at least one thickening agent selected from the group consisting of hydroxypropylmethyl cellulose and xanthan gum.

7. The foam formulation of claim 1, further comprising a stabilizer comprising pentylene glycol.

8. The foam formulation of claim 1, further comprising one or more components selected from the group consisting of shea butter, squalane, and ceramide 3.

9. The foam formulation of claim 1, wherein the membrane-forming substances have an HLB value between 9 and 11.

10. The foam formulation of claim 1, wherein the formulation is a foam cream.

* * * * *